United States Patent
Rummakko et al.

(10) Patent No.: US 8,044,038 B2
(45) Date of Patent: Oct. 25, 2011

(54) CRYSTALLIZATION PROCESS OF QUETIAPINE HEMIFUMARATE

(75) Inventors: Petteri Rummakko, Espoo (FI); Arne Grumann, Kauniainen (FI); Soini Huhta, Espoo (FI); Tuomas Koiranen, Helsinki (FI)

(73) Assignee: Fermion Oy, Espoo (FI)

( * ) Notice: Subject to any disclaimer, the term of this patent is extended or adjusted under 35 U.S.C. 154(b) by 846 days.

(21) Appl. No.: 11/992,223

(22) PCT Filed: Sep. 28, 2006

(86) PCT No.: PCT/FI2006/000318
§ 371 (c)(1),
(2), (4) Date: Mar. 19, 2008

(87) PCT Pub. No.: WO2007/036599
PCT Pub. Date: Apr. 5, 2007

(65) Prior Publication Data
US 2009/0118497 A1    May 7, 2009

Related U.S. Application Data

(60) Provisional application No. 60/722,017, filed on Sep. 30, 2005.

(51) Int. Cl.
*A61P 25/18* (2006.01)
*A61K 31/554* (2006.01)
*C07D 281/16* (2006.01)

(52) U.S. Cl. .................................. 514/211.13; 540/551

(58) Field of Classification Search ............. 514/211.13; 540/551
See application file for complete search history.

(56) References Cited

U.S. PATENT DOCUMENTS 6,372,734 B1    4/2002    Snape et al.

FOREIGN PATENT DOCUMENTS

| EP | 0 240 228 A1 | 10/1987 |
|---|---|---|
| WO | WO-01/55125 A1 | 8/2001 |
| WO | WO-03/080065 A1 | 10/2003 |
| WO | WO-2004/076431 A1 | 9/2004 |

OTHER PUBLICATIONS

Ravikumar et al., "Quetiapine hemifumarate," Acta Crystallographica Section E: Structure Reports, vol. E61, No. 10, 2005, pp. 3245-3248.

*Primary Examiner* — Brenda Coleman
(74) *Attorney, Agent, or Firm* — Birch, Stewart, Kolasch & Birch, LLP

(57) ABSTRACT

The present invention relates to a process for preparing crystalline quetiapine hemifumarate, which comprises crystallizing or re-crystallizing quetiapine hemifumarate from a mixture of water and a water soluble alcohol.

6 Claims, No Drawings

CRYSTALLIZATION PROCESS OF QUETIAPINE HEMIFUMARATE

This application is a National Stage entry of PCT International Application No. PCT/FI2006/000318 filed on Sep. 28, 2006, and claims priority under 35 U.S.C. §119(e) to Provisional Application No. 60/722,017 filed in the U.S. on Sep. 30, 2005, all of which are hereby expressly incorporated by reference into the present application.

FIELD OF THE INVENTION

The present invention relates to a novel process for the preparation of crystalline quetiapine hemifumarate. More specifically, such crystallization process comprises crystallizing or re-crystallizing quetiapine hemifumarate from a mixture of water and a water soluble alcohol and controlling the crystal size distribution by the ratio of alcohol to water.

BACKGROUND OF THE INVENTION 11-(4-[2-(2-Hydroxyethoxy)ethyl]-1-piperazinyl]dibenzo[b,f]-1,4-thiazepine is a well established drug substance known under the INN name quetiapine. It is used as its hemifumarate salt having the structure or formula (1)

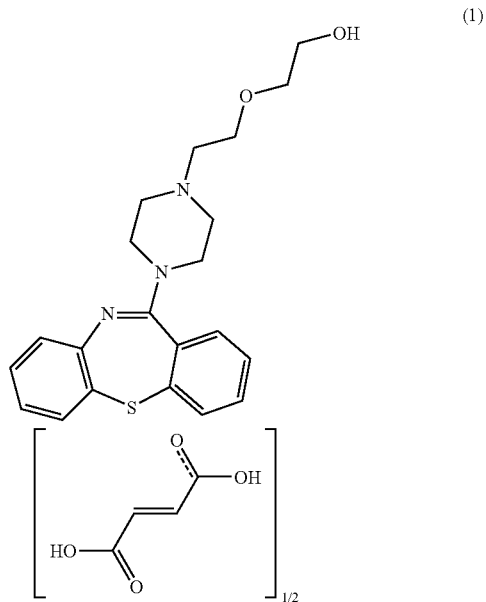

Quetiapine hemifumarate is a psychoactive organic compound that is an antagonist for multiple neurotransmitter receptors in the brain. It is used as an antipsychotic or neuroleptic. Quetiapine hemifumarate, as well as its synthesis, is described, for example, in the European Patent EP 0 240 228 B1. In EP 0 240 228 B1, as well as WO 01/55125, ethanol is used as the solvent component in the crystallization process of quetiapine hemifumarate.

WO 03/080065 relates to new polymorphs of quetiapine hemifumarate and their methods of preparation. It also relates to new methods of preparing the known form of quetiapine hemifumarate and it further provides post-treatment methods, like post-suspension and post-crystallization, for crystalline forms of quetiapine hemifumarate. In said post-crystallization method the crystallization solvent can be selected from lower alkanols, cyclic ethers, ethyl acetate and water.

U.S. Pat. No. 6,372,734 describes the preparation of crystalline quetiapine by crystallizing a quetiapine from a non-aromatic solvent such as ethyl acetate, isobutyl acetate, methyl iso-butylketone or methyl tert-butyl ether, preferably in the absence of water. It further describes how the crystalline quetiapine can then be treated with fumaric acid in a solvent such as an alcohol to obtain the hemifumarate salt.

WO 2004/076431 describes the synthesis of quetiapine and it further describes how the product is converted to the hemifumarate salt which can then be re-crystallized from a solvent that is a lower alkanol, preferably ethanol, or a mixture of water and a dipolar aprotic solvent, preferably dimethyl formamide.

SUMMARY OF THE INVENTION

Applicants have been discovered that it is possible to control the crystal size in the preparation of quetiapine hemifumarate by using water as one of the solvent components in the crystallization process. Accordingly, an object of the present invention is to provide a new process for preparing crystalline quetiapine hemifumarate, which comprises crystallizing or re-crystallizing quetiapine hemifumarate from a mixture of water and a water soluble alcohol.

The discovery of a new solvent composition provides an opportunity to improve the isolation of a pharmaceutical product by controlling the crystal size and furthermore to obtain the final product directly with the desired crystal size needed for the tablet formulation, so that no milling process is needed. As the method for the crystal size control is available, the filtration of the product can be accelerated.

Another object of the present invention is the use of crystalline quetiapine hemifumarate made according to the invention in the preparation of pharmaceuticals.

Additional objects and advantages of the invention will be set forth in part in the description, which follows, and in part will be obvious from the description, or may be learned by practice of the invention. The objects and advantages of the invention will be realized and attained by means of the elements and combinations particularly pointed out in the appended claims.

It is to be understood that the foregoing general description and the following detailed description are exemplary and explanatory only and are not restrictive of the invention as claimed.

DETAILED DESCRIPTION OF THE INVENTION

The present invention provides a novel possibility to control the crystal size of quetiapine hemifumarate in the crystallization process. As used herein and unless otherwise indicated, quetiapine hemifumarate refers to 11-(4-[2-(2-hydroxyethoxy)ethyl]-1-piperazinyl]dibenzo[b,f]-1,4-thiazepine hemifumarate (2:1) salt. The starting material, quetiapine hemifumarate or quetiapine base, for the crystallization can be in any non-crystalline or crystalline form. The crystal size of the starting material is irrelevant because starting material is dissolved before crystallization is started.

Applicants have surprisingly discovered that the control of the crystal size of quetiapine hemifumarate can be based on usage of water as one of the solvent components in the crystallization process when typical crystallization cooling methods are used. Particularly, it has been found that the control of the crystal size of quetiapine hemifumarate is possible by changing the water content of the crystallization solution. Other solvent component used in the crystallization solution can be an alcohol miscible with water.

Thus, the present invention relates to a novel process for the preparation of crystalline quetiapine hemifumarate which comprises crystallizing or re-crystallizing quetiapine hemifumarate from a mixture of water and a water soluble alcohol.

Representative examples of water soluble alcohols include, but are not limited to, methanol, ethanol, n-propanol, iso-propanol, ethylene glycol, and the like.

The particle size of quetiapine hemifumarate crystals can be influenced by controlling the crystallization solvent composition in case of alcohols and water.

Other crystallization conditions have only minor effects to the crystal size of quetiapine hemifumarate.

In general, higher water content in the crystallization solution will result in bigger crystal sizes and lower water content will result in smaller crystal sizes.

The water content of the crystallization solvent will be selected according to the desired crystal size distribution, e,g if water content is between 15 to 20 w-%, 90% of the crystals will be below 244 μm measured by laser diffraction.

Suitable crystallization solvent mixture comprises water and alcohol in a ratio ranging from 100:0 to 8:92 (water:alcohol) volume/volume, preferably in the ratio from 35:65 to 15:85 (water:alcohol).

The typical crystallization process includes the steps of refluxing a solution of quetiapine hemifumarate in a crystallization solvent mixture for a reflux time; using a typical cooling profile; and isolating quetiapine hemifumarate and drying it. The crystallization may be initiated with the aid of seed crystal.

One skilled in the art knows that some of the conditions concerning crystallization can be modified without affecting the crystal size of the quetiapine hemifumarate obtained.

The ratio of quetiapine hemifumarate to treating solvent is not critical. However, typical quetiapine hemifumarate solution (quetiapine in ethanol-water) concentrations in are between 10 w-% to 40 w-%, preferably between 15 to 25 w-%. The skilled in the art will know how to adjust the proportions depending on, for example, the yield compared to the equipment size.

Similarly, the reflux time is not critical. Typically, reflux times of 1 to 4 hours are sufficient.

The temperature of the solution may be decreased during the crystallization. When the typical crystallization cooling profile is used the temperature can be decreased to 0° C. to 20° C. In particular, the temperature of the solution is decreased gradually over a period of time. Thus, in a specific example, the temperature is first decreased to 65° C., seeding is done in 65° C. and kept for 4 hours. Then temperature is further decreased to 40° C. during 4 to 5 hours and then still decreased to 0° C. over a period of 6 to 8 hours. In particular, the temperature is decreased from temperature 65° C. to 0° C. over period of 10 to 13 hours. Where a seed crystal is used it will generally be added to the crystallization mixture when that mixture is at temperature from 35 to 95° C.

The time of crystallization is not critical but can vary from 5 to 20 hours.

Following treatment, the crystalline quetiapine hemifumarate is isolated by suitable means as are known to skilled artisan and routiner alike, for example, filtration (pressure or suction), centrifugation or decanting. The isolated solid quetiapine hemifumarate can be dried at atmospheric or at reduced pressure in different temperatures depending on the solvent vapour pressures. The time of drying is irrelevant.

The invention will be further clarified by the following nonlimiting examples, which are intended to be purely exemplary of the invention. The starting material, quetiapine hemifumarate or quetiapine base, for the crystallization can be made by any method described in the literature, e.g. as in EP 0240228.

EXAMPLE 1

Crude and dried quetiapine hemifumarate (10 g), ethanol (36.4 g) and water (3.6 g) were charged into reactor 1. Crude and dried quetiapine hemifumarate (10 g), ethanol (30.8) g) and water (9.2 g) were charged into reactor 2. Crude and dried quetiapine hemifumarate (10 g) and water (40 g) were charged into reactor 3. Each composition was treated in a following way.

The mixtures in reactors 1, 2 and 3 were warmed up to 93° C. until crystals were completely dissolved. The solutions were cooled to 65° C. and then they were seeded. The solutions were kept at 65° C. for 4 hours. They were cooled further to 57° C. during 2 hours (4° C./h), then cooled to 40° C. during 2.5 hours (6.8° C./h), and finally they were cooled to 0° C. during 7 hours (5.7° C./h). The crystals were filtrated at 0° C., and they were dried at 65° C. in laboratory vacuum dryer.

EXAMPLE 2

Crude and dried quetiapine hemifumarate (36.3 g) and water (145.2 g) were charged into a reactor. The mixture in the reactor was warmed to reflux. The solution was cooled to 85° C. and then it was seeded. The solution was kept at 85° C. for 4 hours. It was cooled further to 57° C. during 4 hours (7° C./h), then cooled to 40° C. during 2.5 hours (6.8° C./h), and finally it was cooled to 0° C. during 7 hours (5.7° C./h). The crystals were filtrated at 0° C., and they were dried at 65° C. in laboratory vacuum dryer.

Same crude quetiapine hemifumarate was used in Examples 1 and 2.

EXAMPLE 3

Crude and dried quetiapine hemifumarate (2.5 g), ethanol (9 g) and water (1 g) were charged into reactor. The mixture in reactor was warmed to reflux. The solution was cooled to 66° C. and then it was seeded. The solution was cooled further to 0° C. during 10 hours (6.6° C./h). The crystals were filtrated at 0° C., and they were dried at 80° C. in laboratory vacuum dryer.

EXAMPLE 4

Crude and dried quetiapine hemifumarate (2.5 g) and water (10 g) were charged into reactor. The mixture in reactor was warmed to reflux. The solution was cooled to 85° C. and then it was seeded. The solution was cooled further to 0° C. during 10 hours (8.5° C./h). The crystals were filtrated at 0° C., and they were dried at 80° C. in laboratory vacuum dryer.

Same crude quetiapine hemifumarate was used in Examples 3 and 4.

Yields in presented examples were within 83-93%. The results of examples 1 to 4 are summarized in Table 1.

TABLE 1

Dependence of the crystal size (longest dimension) on solvent composition (particle size determination by microscope)

|  | Quetiapine conc. in solution, w-% | Ethanol-water solvent composition, w-% | Size of crystals, μm |
|---|---|---|---|
| Example 1: Reactor 1 | 20 | 91 | 10-20 |
| Example 1: Reactor 2 | 20 | 77 | 50-100 |
| Example 1: Reactor 3 | 20 | 0 | 50-300 |
| Example 2 | 20 | 0 | 50-300 |

TABLE 1-continued

Dependence of the crystal size (longest dimension) on solvent composition (particle size determination by microscope)

| | Quetiapine conc. in solution, w-% | Ethanol-water solvent composition, w-% | Size of crystals, μm |
|---|---|---|---|
| Example 3 | 20 | 90 | 10-100 |
| Example 4 | 20 | 0 | 20-200 |

In examples 1 to 4 the crystal size analysis was performed using a light microscope and analysis was made by visual observation. Zeiss Immersol 518 N oil was used as a sample media. As used in connection with examples 1 to 4 the term "size of crystals" means that at least 90% by volume of crystal particles has a length within the stated range.

As can be seen clearly from these data, size of crystals depends on the solvent composition in case of alcohols and water, for example, when the ratio of alcohol to water changes from 91:9 to 77:22, the size of crystals increases from 10-20 microns to 50-100 microns respectively. Whereas cooling rate has only minor effect to the crystal size (comparison of Examples 3 and 4).

EXAMPLE 5

Crude quetiapine hemifumarate (60 g) containing ethanol (4.6 g), water (44.3 g) and ethanol (177.3 g) were charged into reactor with 1.7 g active charcoal and 0.8 g celite. The mixture in reactor was warmed to 80° C. and the solution was filtrated with pressure filter. The clear solution was cooled to 40° C. and then it was seeded. The solution was mixed 15 minutes, and then cooled to 30° C. during 30 minutes (20° C./h). The solution was further cooled to 0° C. during 6 hours (5° C./h). The crystals were filtrated and washed with 70 ml ethanol at 0° C. Crystals were dried at 60° C. in vacuum dryer. Yield was 85%.

EXAMPLE 6

Crude quetiapine hemifumarate (60 g) containing ethanol (4.6 g), water (33.2 g) and ethanol (188.4 g) were charged into reactor with 1.7 g active charcoal and 0.8 g celite. The mixture in reactor was warmed to 80° C. and the solution was filtrated with pressure filter. The clear solution was cooled to 40° C. and then it was seeded. The solution was mixed 15 minutes, and then cooled to 30° C. during 30 minutes (20° C./h). The solution was further cooled to 0° C. during 6 hours (5° C./h). The crystals were filtrated and washed with 70 ml ethanol at 0° C. Crystals were dried at 60° C. in vacuum dryer. Yield was 87%.

The results of the examples 5 and 6 are summarized in Table 2.

TABLE 2

Dependence of the crystal particle size on solvent composition (crystal size determined with laser diffraction Coulter LS 230 (PIL))

| | Quetiapine conc. in solution, w-% | Ethanol-water solvent composition, w-% | Size of crystals, μm |
|---|---|---|---|
| Example 5 | 20 | 80 | 90% < 244 |
| | | | 50% < 83 |
| | | | 10% < 25 |
| | | | Mean: 108 |
| Example 6 | 20 | 85 | 90% < 148 |
| | | | 50% < 44 |
| | | | 10% < 14 |
| | | | Mean: 60 |

In examples 5 and 6 the crystal size analysis was performed using laser diffraction analyser (light scattering). Volume cell was 15 ml, optical length 0.6 cm, obscuration about 8 to 12%. Methyl siloxane was used as a dispersant. The sample is allowed to stir for 4-5 minutes before running the analysis.

Those skilled in the art will appreciate that the embodiments described in this application could be modified without departing from the inventive concept. Those skilled in the art also understand that the invention is not limited to the particular disclosed embodiments, but is intended to also cover modifications to the embodiments that are within the spirit and scope of the invention.

The invention claimed is:

1. A process for preparing crystalline quetiapine hemifumarate, which comprises crystallizing or re-crystallizing quetiapine hemifumarate from a mixture of water and a water soluble alcohol, wherein the mixture of water and the water-soluble alcohol comprises water and alcohol in a ratio from 35:65 to 15:85.

2. A process according to claim 1, wherein the water-soluble alcohol is methanol, ethanol, n-propanol, iso-propanol or ethylene glycol.

3. A process according to claim 2, wherein the water-soluble alcohol is ethanol.

4. A process of any of claims 1 to 3 wherein 90% of resulting crystals have a particle size less than 244 μm, analysed by laser diffraction.

5. A process of any of claims 1 to 3 wherein the alcohol is used at least 80% in the crystallization solvent and 90% of resulting crystals have a particle size less than 244 μm, analysed by laser diffraction.

6. A method of making a pharmaceutical composition comprising mixing crystalline quetiapine hemifumarate made by claim 4 with a pharmaceutically acceptable carrier.

* * * * *